(12) United States Patent
Laughton et al.

(10) Patent No.: US 11,844,819 B2
(45) Date of Patent: *Dec. 19, 2023

(54) OIL EXTRACT OF CANNABIS AND METHOD FOR OBTAINING

(71) Applicant: Concept Matrix Solutions, Newbury Park, CA (US)

(72) Inventors: Toby W. Laughton, Woodland Hills, CA (US); Darren J. Nist, Riverside, CA (US); Steven M. Shatkin, Mammoth Lakes, CA (US); Tony LaRosa, Woodland Hills, CA (US); David Reid, Woodland Hills, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/067,944

(22) Filed: Dec. 19, 2022

(65) Prior Publication Data

US 2023/0131963 A1 Apr. 27, 2023

Related U.S. Application Data

(63) Continuation of application No. 17/177,532, filed on Feb. 17, 2021, now Pat. No. 11,541,089.

(60) Provisional application No. 62/978,603, filed on Feb. 19, 2020.

(51) Int. Cl.
*A61K 36/185* (2006.01)
*A61K 31/352* (2006.01)
*B01D 11/02* (2006.01)
*B01D 29/27* (2006.01)

(52) U.S. Cl.
CPC .......... *A61K 36/185* (2013.01); *A61K 31/352* (2013.01); *B01D 11/0288* (2013.01); *B01D 29/27* (2013.01); *A61K 2236/15* (2013.01); *A61K 2236/35* (2013.01); *A61K 2236/53* (2013.01)

(58) Field of Classification Search
None
See application file for complete search history.

(56) References Cited

FOREIGN PATENT DOCUMENTS

WO 2019070885 A1 4/2019

OTHER PUBLICATIONS

U.S. Patent and Trademark Office, "Notice of Allowance and Fee(s) Due," U.S. Appl. No. 17/177,532, dated Aug. 22, 2022, 13 pgs.

*Primary Examiner* — Michael V Meller
(74) *Attorney, Agent, or Firm* — Carlson, Caspers, Vandenburgh & Lindquist P.A.

(57) ABSTRACT

The present invention provides for a method for obtaining an oil extract of *cannabis*. The method includes: (a) contacting *cannabis* biomass and an edible oil; (b) pressing between a pair of plates to provide spent *cannabis* and an oil extract of *cannabis*; and (c) separating the spent *cannabis* biomass and the oil extract of *cannabis*.

19 Claims, No Drawings

OIL EXTRACT OF CANNABIS AND METHOD FOR OBTAINING

RELATED U.S. APPLICATION DATA

This application is a continuation of U.S. patent application Ser. No. 17/177,532 filed on Feb. 17, 2021, now U.S. Pat. No. 11,541,089, issued on Jan. 3, 2023, which claims the benefit of priority from U.S. Provisional Patent Application 62/978,603 filed on Feb. 19, 2020, the contents of which are incorporated by reference herein in their entirety.

SUMMARY OF THE INVENTION

The present invention provides for a method for obtaining an oil extract of *cannabis*. The method includes: (a) contacting *cannabis* biomass and an edible oil; (b) pressing between a pair of plates, the *cannabis* biomass and an edible oil, to provide spent *cannabis* and an oil extract of *cannabis*; and (c) separating the spent *cannabis* biomass and the oil extract of *cannabis*.

The present invention also provides for another method for obtaining an oil extract of *cannabis*. The method includes: (a) contacting *cannabis* biomass and an edible oil; (b) pressing the *cannabis* biomass and the edible oil in an enclosure, sufficient to release from the *cannabis* biomass into the edible oil, one or more cannabinoids, one or more terpenes, or a combination thereof, to provide spent *cannabis* and an oil extract of *cannabis*; and (c) separating the spent *cannabis* biomass and the oil extract of *cannabis*. The oil extract of *cannabis* includes one or more cannabinoids, one or more terpenes, or a combination thereof. The method can optionally further include before the contacting in step (a), the step of reducing the size of the *cannabis* biomass. The method can optionally further include after the contacting in step (a) and before the pressing in step (b), the step of steeping the *cannabis* biomass and the edible oil. The method can optionally further include after the separating in step (c), the step of purifying the oil extract of *cannabis*.

The present invention also provides for another method for obtaining an oil extract of *cannabis*. The method includes: (a) reducing the size of *cannabis* biomass; (b) contacting *cannabis* biomass and an edible oil; (c) steeping the *cannabis* biomass and the edible oil; (d) pressing the biomass and the edible oil in an enclosure, sufficient to release from the *cannabis* biomass into the edible oil, one or more cannabinoids, one or more terpenes, or a combination thereof, to provide spent *cannabis* and an oil extract of *cannabis*; (e) separating the spent *cannabis* biomass and the oil extract of *cannabis*; and (f) purifying the oil extract of *cannabis*. The oil extract of *cannabis* includes one or more cannabinoids, one or more terpenes, or a combination thereof.

The present invention also provides for another method for obtaining a purified oil extract of *cannabis*. The method includes: (a) reducing the size of *cannabis*; (b) contacting the *cannabis* biomass and the edible oil in an enclosure containing a food grade mesh nylon bag; (c) steeping the *cannabis* biomass and the edible oil; (d) pressing between two substantially flat plates, the enclosure and contents therein, sufficient to release from the *cannabis* biomass into the edible oil, one or more cannabinoids, one or more terpenes, or a combination thereof, to provide spent *cannabis* and an oil extract of *cannabis*; (e) separating the spent *cannabis* biomass and the oil extract of *cannabis*; (f) collecting the oil extract of *cannabis* in a receptacle; (g) contacting the oil extract of *cannabis* with carbon black, to provide a purified oil extract of *cannabis*; and (h) separating the carbon black from the purified oil extract of *cannabis*.

The present invention also provides for another method for obtaining a purified oil extract of *cannabis*. The method includes: (a) reducing the size of *cannabis* biomass such that at least 90 wt. % of the *cannabis* biomass is less than 2.5 mm; (b) contacting the *cannabis* biomass and the edible oil in an enclosure containing a food grade mesh nylon bag; (c) steeping at a temperature of 50-180° C. the *cannabis* biomass and the edible oil; (d) pressing between two substantially flat plates, at a temperature of 20-150° C. and a pressure of 1,000-100,000 psi, the enclosure and contents therein, sufficient to release from the *cannabis* biomass into the edible oil, one or more cannabinoids, one or more terpenes, or a combination thereof, to provide spent *cannabis* and an oil extract of *cannabis*; (e) separating the spent *cannabis* biomass and the oil extract of *cannabis*; (f) collecting the oil extract of *cannabis* in a receptacle; (g) contacting the oil extract of *cannabis* with carbon black in an amount of 0.5±0.2 grams of carbon black per 100 grams of the oil extract of *cannabis*, to provide a purified oil extract of *cannabis*; and (h) separating the carbon black from the purified oil extract of *cannabis*.

The present invention also provides for an oil extract of *cannabis* obtained from the method described herein. The present invention also provides for a purified oil extract of *cannabis* obtained from the method described herein.

Across multiple embodiments, the method described herein can independently possess one or more advantages. For example, in specific embodiments, the method is carried out on a relatively large scale (e.g., up to 40 ounces of *cannabis* biomass is employed per batch). In specific embodiments, the oil extract of *cannabis* obtained is a full-spectrum extract of *cannabis* or a broad-spectrum extract of *cannabis*. Alternatively, in specific embodiments, the oil extract of *cannabis* obtained is an isolate of *cannabis* (e.g., CBD isolate and/or THC isolate). Alternatively, in specific embodiments, the oil extract of *cannabis* obtained includes phytocannabinoid rich hemp oil. Alternatively, in specific embodiments, the oil extract of *cannabis* obtained includes full extract *cannabis* oil (FECO). In specific embodiments, the oil extract of *cannabis* is obtained in a relatively large yield (e.g., up to 160 grams of oil extract of *cannabis* is obtained, per pound of *cannabis* biomass). In specific embodiments, the oil extract of *cannabis* is obtained in a relatively high concentration (e.g., the oil extract of *cannabis* includes up to 35 wt. % of cannabinoids, terpenes, or combination thereof). In specific embodiments, the oil extract of *cannabis* is obtained containing THC in a relatively high concentration (e.g., the oil extract of *cannabis* includes up to 30.5 wt. % THC). In specific embodiments, the oil extract of *cannabis* is obtained in a relatively high purity (e.g., the oil extract of *cannabis* includes less 1 wt. % terpenes). In specific embodiments, the oil extract of *cannabis* is a THC isolate obtained in a relatively high purity (e.g., the oil extract of *cannabis* includes THC and further includes less 1 wt. % CBD). In specific embodiments, the oil extract of *cannabis* is obtained in a relatively high purity (e.g., the oil extract of *cannabis* includes less than 0.1 wt. % pesticides, less than 0.1 wt. % heavy metals, less than 0.1 wt. % microbials, less than 0.1 wt. % volatile organic compounds (VOCs), and/or less than 1 wt. % chlorophylls). In specific embodiments, the method is carried out in the absence of a polar liquid organic solvent (e.g., chloroform, methylene chloride, ethyl acetate, ethanol, and/or methanol). In specific embodiments, the method is carried out in the absence of volatile organic compound (VOC) solvent. In specific embodiments, the method is carried out in the absence of a supercritical fluid extraction solvent (e.g., carbon dioxide, butane, propane, and/or ethanol). In specific embodiments, the method is carried out in the absence of a pressurized vessel (e.g., supercritical fluid extraction container). In specific embodiments, the method is carried out in a relatively short period of time (e.g., less than 120 minutes). In specific embodiments, the method is carried out multiple times (e.g., at least 5) within an 8-hour period of time. In specific embodiments, the oil extract of *cannabis* is suitable for oral administration to a human. In specific embodiments, the oil extract of *cannabis* is suitable for topical administration to a human. In specific embodiments, the oil extract of *cannabis* is suitable for oral administration to a human, without purification. In specific embodiments, the oil extract of *cannabis* is suitable for topical administration to a human, without purification. In specific embodiments, the purified oil extract of *cannabis* obtained therein (i.e., oil extract of *cannabis* which is subsequently purified to a desired level of purity) is suitable for administration (e.g., oral and/or topical) to a human.

DETAILED DESCRIPTION OF THE INVENTION

The present invention provides for a method for obtaining an oil extract of *cannabis*. The method can be carried out in a batch mode, on a relatively large scale, and in a relatively short period of time. Depending on the processing parameters employed, a variety of products can be obtained (e.g., full-spectrum extract of *cannabis*, broad-spectrum extract of *cannabis*, CBD isolate, THC isolate, phytocannabinoid rich hemp oil, full extract *cannabis* oil (FECO), etc.). The oil extract of *cannabis* can be obtained in a relatively large yield and high purity. Additionally, the oil extract of *cannabis* obtained therein is suitable for administration (e.g., oral and/or topical) to a human, or the oil extract of *cannabis* can subsequently be purified (purified oil extract of *cannabis*) to a desired level of purity, to also be suitable for administration (e.g., oral and/or topical) to a human.

The term "*cannabis*" refers to a genus of flowering plants in the family Cannabaceae. The number of species within the genus is disputed. Three species may be recognized: *Cannabis sativa, Cannabis indica,* and *Cannabis ruderalis; C. ruderalis* may be included within *C. sativa;* all three may be treated as subspecies of a single species, *C. sativa;* or *C. sativa* may be accepted as a single undivided species. The plant is also known as hemp, although this term is often used to refer only to varieties of *Cannabis* cultivated for non-drug use. *Cannabis* has long been used for hemp fiber, hemp seeds and their oils, hemp leaves for use as vegetables and as juice, medicinal purposes, and as a recreational drug. Industrial hemp products are made from *cannabis* plants selected to produce an abundance of fiber.

The term "biomass" refers to a plant material, in whole or in part, useful as a starting material (raw material) in a manufacturing process. As such, "*cannabis* biomass" refers to a *cannabis* plant material, in whole or in part, useful as a starting material (raw material) in a manufacturing process.

The term "full-spectrum extract" or "whole plant extract" refers to an extract of *cannabis* that maintains the full profile of the *cannabis* plant. The full-spectrum extract of *cannabis* typically contains a variety of cannabinoids, including THC, THCa, CBD, CBDa, CBG, and CBN, as well as terpenes and other compounds such as flavonoids, proteins, phenols, sterols, and esters. Full-spectrum extracts are notoriously difficult to produce. While you need to keep as many of the desirable compounds as possible, you also want to rid the extract of unnecessary components.

The term "broad-spectrum extract" refers to an extract of *cannabis* that maintains a broad profile of the *cannabis* plant, but the profile is more limiting than the full-spectrum extract. The broad-spectrum extract of *cannabis* typically contains a variety of cannabinoids, including THC, CBD, and CBN, as well as terpenes. Broad-spectrum extracts are difficult to produce. While you need to keep as many of the desirable compounds as possible, you also want to rid the extract of unnecessary components.

The term "isolate" refers to a relatively pure extract of *cannabis*. The purity can be at least 90 wt. % pure, at least 95 wt. % pure, at least 98 wt. % pure, or at least 99 wt. % pure. The isolate can be, e.g., a THC isolate, CBD isolate, or CBN isolate.

The term "phytocannabinoid rich hemp oil" (or PCR hemp oil) refers to a full spectrum extract that in addition to cannabinoids, terpenes, and flavonoids, also contains vitamins, minerals, fatty acids, phytonutrients, and other materials naturally present in the hemp plant.

The term "full extract *cannabis* oil" (or FECO) refers to an extract from the *cannabis* flowers/buds and optionally the leaves.

The term "cannabinoid" refers to a class of diverse chemical compounds that act on cannabinoid receptors on cells that repress neurotransmitter release in the brain. These receptor proteins include the endocannabinoids (produced naturally in the body by humans and animals), the phytocannabinoids (found in *Cannabis* and some other plants), and synthetic cannabinoids (manufactured chemically). The most notable cannabinoid is the phytocannabinoid 49-tetrahydrocannabinol (THC), the primary psychoactive compound of *Cannabis*. Cannabidiol (CBD) is another major constituent of the plant, representing up to 40% in extracts of the plant resin. There are at least 85 different cannabinoids isolated from *Cannabis*, exhibiting varied effects.

| Cannabinoids isolated from *Cannabis* |
|---|
| 1. Cannabigerol ((E)-CBG-C5) |
| 2. Cannabigerol monomethyl ether ((E)-CBGM-C5 A) |
| 3. Cannabinerolic acid A ((Z)-CBGA-C5 A) |
| 4. Cannabigerovarin ((E)-CBGV-C3) |
| 5. Cannabigerolic acid A ((E)-CBGA-C5 A) |
| 6. Cannabigerolic acid A monomethyl ether ((E)-CBGAM-C5 A) |
| 7. Cannabigerovarinic acid A ((E)-CBGVA-C3 A) |
| 8. (±)-Cannabichromene (CBC-C5) |
| 9. (+)-Cannabichromenic acid ACBCA-C5 A |
| 10. (+)-Cannabivarichromene or (+)-Cannabichromevarin (CBCV-C3) |
| 11. (+)-Cannabichromevarinic acid A (CBCVA-C3 A) |
| 12. (−)-Cannabidiol (CBD-C5) |
| 13. Cannabidiol momomethyl ether (CBDM-C5) |
| 14. Cannabidiol-C4 (CBD-C4) |
| 15. (−)-Cannabidivarin CBDV-C3 |
| 16. Cannabidiorcol (CBD-C1) |
| 17. Cannabidiolic acid (CBDA-C5) |
| 18. Cannabidivarinic acid (CBDVA-C3) |
| 19. Cannabinodiol (CBND-C5) |
| 20. Cannabinodivarin (CBND-C3) |
| 21 Δ9-Tetrahydrocannabinol (Δ9-THC-C5) |
| 22. Δ9-Tetrahydrocannabinol-C4 (Δ9-THC-C4) |
| 23. Δ9-Tetrahydrocannabivarin (Δ9-THCV-C3) |
| 24. Δ9-Tetrahydrocannabiorcol (Δ9-THCO-C1) |
| 25. Δ9-Tetrahydro-cannabinolic acid A (Δ9-THCA-C5 A) |
| 26. Δ9-Tetrahydro-cannabinolic acid B (Δ9-THCA-C5 B) |
| 27. Δ9-Tetrahydro-cannabinolic acid-C4A and/or B (Δ9-THCA-C4A and/or B) |
| 28. Δ9-Tetrahydro-cannabivarinic acid A (Δ9-THCVA-C3A) |
| 29. Δ9-Tetrahydro-cannabiorcolic acid A and/or B (Δ9-THCOA-C1A and/or B) |

| Cannabinoids isolated from Cannabis |
| --- |
| 30. (−)-Δ8-trans-(6aR,10aR)-Δ8-Tetrahydrocannabinol (Δ8-THC-C5) |
| 31. (−)-Δ8-trans-(6aR,10aR)-Tetrahydrocannabinolic acid A (Δ8-THCA-C5 A) |
| 32. (−)-(6aS,10aR)-Δ9-Tetrahydrocannabinol ((−)-cis-Δ9-THC-C5) |
| 33. Cannabinol (CBN-C5) |
| 34. Cannabinol-C4 (CBN-C4) |
| 35. Cannabivarin (CBN-C3) |
| 36. Cannabinol-C2 (CBN-C2) |
| 37. Cannabiorcol (CBN-C1) |
| 38. Cannabinolic acid A (CBNA-C5 A) |
| 39. Cannabinol methyl ether (CBNM-C5) |
| 40. (−)-(9R,10R)-trans-Cannabitriol ((−)-trans-CBT-C5) |
| 41. (+)-(9S,10S)-Cannabitriol ((+)-trans-CBT-C5) |
| 42. (±)-(9R,10S/9S,10R)-Cannabitriol ((±)-cis-CBT-C5) |
| 43. (−)-(9R,10R)-trans-10-O-Ethyl-cannabitriol ((−)-trans-CBT-OEt-C5) |
| 44. (±)-(9R,10R/9S,10S)-Cannabitriol-C3 ((±)-trans-CBT-C3) |
| 45. 8,9-Dihydroxy-Δ6a(10a)-tetrahydrocannabinol (8,9-Di-OH-CBT-C5) |
| 46. Cannabidiolic acid A cannabitriol ester (CBDA-C5 9-OH-CBT-C5 ester) |
| 47. (−)-(6aR,9S,10S,10aR)-9,10-Dihydroxy-hexahydrocannabinol, Cannabiripsol (Cannabiripsol-C5) |
| 48. (−)-6a,7,10a-Trihydroxy-Δ9-tetrahydrocannabinol ((−)-Cannabitetrol) |
| 49. 10-Oxo-Δ6a(10a)-tetrahydrocannabinol (OTHC) |
| 50. (5aS,6S,9R,9aR)-Cannabielsoin (CBE-C5) |
| 51. (5aS,6S,9R,9aR)-C3-Cannabielsoin (CBE-C3) |
| 52. (5aS,6S,9R,9aR)-Cannabielsoic acid A (CBEA-C5 A) |
| 53. (5aS,6S,9R,9aR)-Cannabielsoic acid B (CBEA-C5 B) |
| 54. (5aS,6S,9R,9aR)-C3-Cannabielsoic acid B (CBEA-C3 B) |
| 55. Cannabiglendol-C3 (OH-iso-HHCV-C3) |
| 56. Dehydrocannabifuran (DCBF-C5) |
| 57. Cannabifuran (CBF-C5) |
| 58. (−)-Δ7-trans-(1R,3R,6R)-Isotetrahydrocannabinol |
| 59. (±)-Δ7-1,2-cis-(1R,3R,6S/1S,3S,6R)-Isotetrahydro-cannabivarin |
| 60. (−)-Δ7-trans-(1R,3R,6R)-Isotetrahydrocannabivarin |
| 61. (±)-(1aS,3aR,8bR,8cR)-Cannabicyclol (CBL-C5) |
| 62. (±)-(1aS,3aR,8bR,8cR)-Cannabicyclolic acid A (CBLA-C5 A) |
| 63. (±)-(1aS,3aR,8bR,8cR)-Cannabicyclovarin (CBLV-C3) |
| 64. Cannabicitran (CBT-C5) |
| 65. Cannabichromanone (CBCN-C5) |
| 66. Cannabichromanone-C3 (CBCN-C3) |
| 67. Cannabicoumaronone (CBCON-C5) |
| 68. Cannabielsoin acid A (CBEA-A) |
| 69. 10-Ethoxy-9-hydroxy-delta-6a-tetrahydrocannabinol |
| 70. Cannabitriolvarin (CBTV) |
| 71. Delta-9-tetrahydrocannabiorcolic acid (THCA-C1) |
| 72. Delta-7-cis-iso-tetrahydrocanna |
| 73. Cannabichromanon (CBCF) |

| Structure of common cannabinoids |
| --- |

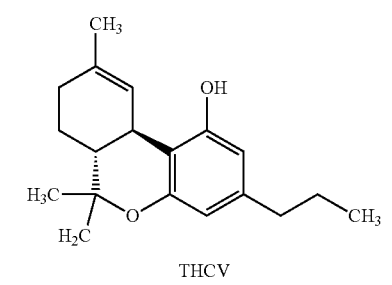

CBD

| Structure of common cannabinoids |
| --- |

CBDA

CBDVA-OMe

THC

THCA

THCV

| Structure of common cannabinoids | Structure of common cannabinoids |
|---|---|
| 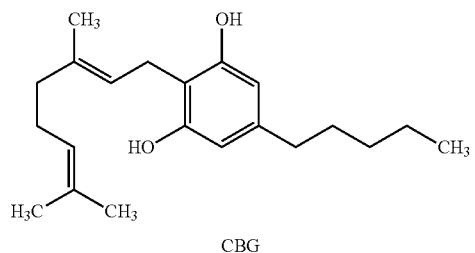 [SMILES: CCCCCc1cc(O)c(C/C=C(\C)CCC=C(C)C)c(O)c1 ; "CBG"]<br>CBG | 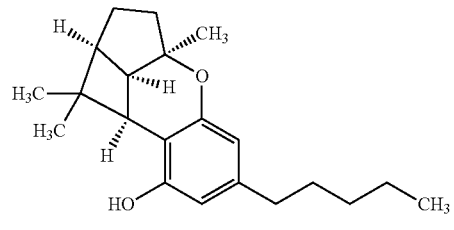<br>CBL |
| 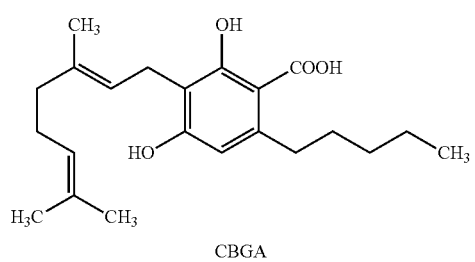 [SMILES: CCCCCc1cc(O)c(C/C=C(\C)CCC=C(C)C)c(O)c1C(=O)O ; "CBGA"]<br>CBGA | 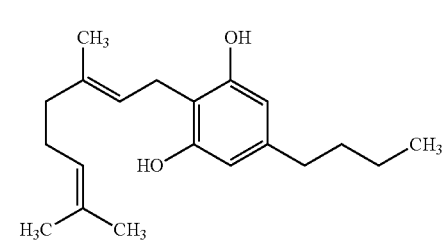<br>CBGB |
| 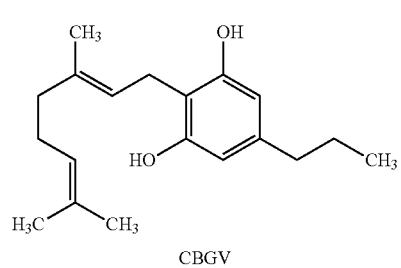 [SMILES: CCCc1cc(O)c(C/C=C(\C)CCC=C(C)C)c(O)c1 ; "CBGV"]<br>CBGV | 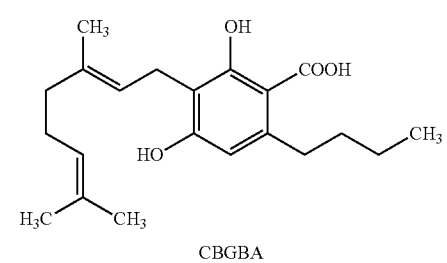<br>CBGBA |
| 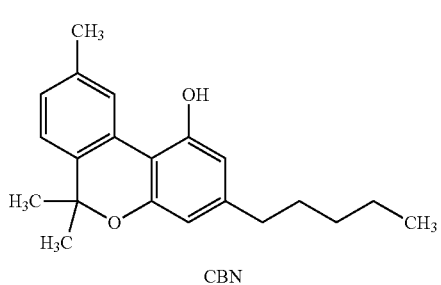<br>CBN | 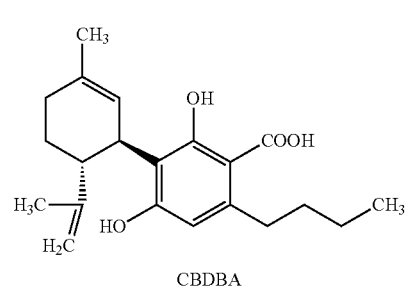<br>CBDBA |
| 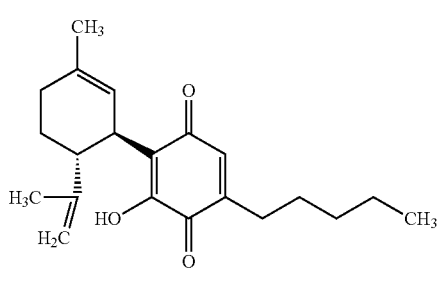<br>CBQ | 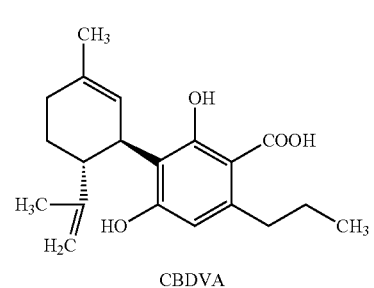<br>CBDVA |
| 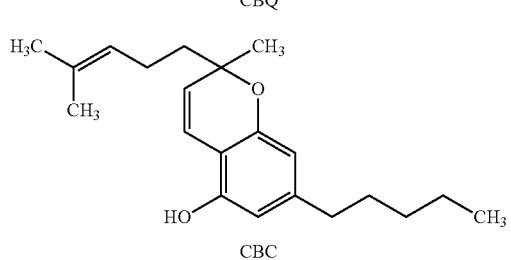<br>CBC | |

-continued

Structure of common cannabinoids

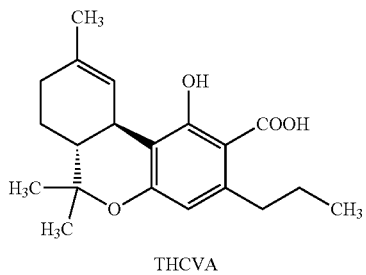

THCVA

The term "terpene" refers to a hydrocarbon or derivative thereof, found as a natural product and biosynthesized by oligomerization of isoprene units. A terpene can be acyclic, monocyclic, bicyclic, or multicyclic. Examples include, e.g., sesquiterpenes (e.g., (−)-β-caryophyllene, humulene, vetivazulene, guaiazulene, longifolene, copaene, and patchoulol), monoterpenes (e.g., limonene and pulegone), monoterpenoids (e.g., carvone), diterpenes (e.g., taxadiene), and triterpenes (e.g., squalene, betulin, betulinic acid, lupane, lupeol, betulin-3-caffeate, allobetulin, and cholesterol). The following are examples of terpenes present in *cannabis* biomass.

| Terpene |
| --- |
| β-myrcene |
| δ-limonene |
| β-caryophyllene |
| β-pinene |
| α-pinene |
| α-terpineol |
| α-humulene |
| camphene |
| fenchone |
| terpinolene |
| α-terpinene |
| 3-carene |
| α-phellandrene |
| borneol |
| fenchol |
| ocimene |
| valencene |

As used herein, "oil" refers to a nonpolar chemical substance that is a viscous liquid at ambient temperatures and is both hydrophobic (does not mix with water, literally "water fearing") and lipophilic (mixes with other oils, literally "fat loving"). Oils have a high carbon and hydrogen content and are usually flammable and surface active. Most oils are unsaturated lipids that are liquid at room temperature.

Within the context of the present invention, the oil can be a cooking oil or an edible oil. As used herein, a "cooking oil" or "edible oil" refers to a plant, animal, or synthetic fat used in frying, baking, and other types of cooking. It is also used in food preparation and flavoring not involving heat, such as salad dressings and bread dippings like bread dips, and may be called edible oil. Cooking oil is typically a liquid at room temperature, although some oils that contain saturated fat, such as coconut oil, palm oil and palm kernel oil are solid. There is a wide variety of cooking oils from plant sources such as olive oil, palm oil, soybean oil, canola oil (rapeseed oil), corn oil, peanut oil and other vegetable oils, as well as animal-based oils like butter and lard.

It is appreciated that those of skill in the art understand that the method for obtaining an oil extract of *cannabis*, as described herein, is not a hot solvent extraction that employs water or an organic solvent (e.g., polar liquid organic solvent, volatile organic solvent, etc.), nor does it employ a subcritical fluid extraction utilizing a pressurized vessel and a supercritical fluid extraction solvent system (e.g., carbon dioxide). Instead, the method for obtaining an oil extract of *cannabis*, as described herein, employs an edible oil.

As used herein, an "extract" refers to a substance obtained from the extraction of a raw material, using a solvent. Within the context of the present invention, the extraction is carried out by soaking, in an enclosure (e.g., mesh nylon bag), *cannabis* biomass in the edible oil. The enclosure is then pressed, thereby releasing an oil extract of *cannabis* from the spent *cannabis* biomass. In specific embodiments, after the soaking and prior to the pressing, the *cannabis* biomass can be reduced to a desired size (e.g., average particle size of less than 2.5 mm). In other specific embodiments, the *cannabis* biomass can be reduced to a desired size (e.g., average particle size of less than 2.5 mm) prior to the soaking. Additionally, in specific embodiments, the *cannabis* biomass can be steeped in the edible oil, such that the soaking is carried out at an elevated temperature (e.g., up to 110° C.) for an extended period of time (e.g., up to 24 hours). Additionally, in specific embodiments, the pressing can be carried out at an elevated temperature (e.g., up to 65-110° C.). Alternatively, in specific embodiments, the pressing can be carried out at room temperature (e.g., 18-21° C.), such that it is a cold press.

As used herein, "steeped" or "steeping" refers to the soaking of a raw material in a hot solvent to obtain an extract. Within the context of the present invention, the steeping is carried out by soaking *cannabis* biomass in an edible oil at an elevated temperature. For example, the temperature of the edible oil can be up to 100° C., up to 125° C., up to 150° C., or up to up to 175° C. Likewise, the steeping can be carried out for an extended period of time. For example, the steeping can be carried out for about 5-25 minutes, up to 1 hour, up to 12 hours, or up to 24 hours.

As used herein, "size" refers to the magnitude or dimensions of an item. More specifically, geometrical size (or spatial size) can refer to linear dimensions (length, width, height, diameter, perimeter), area, or volume of an item. Within the context of the present invention, the size refers to the linear dimensions of the *cannabis* biomass. In specific embodiments, the *cannabis* biomass can be reduced to a desired size (diameter). This size reduction can be carried out, e.g., by blending, grinding, pulverizing, mincing, liquefying, cutting, macerating, and/or chopping the *cannabis* biomass. The resulting *cannabis* biomass will have a desired size, as measured by the average particle size. There are several methods for measuring particle size and particle size distribution. Within the context of the present invention, "average particle size" refers to a weight average and the linear dimension(s) can be measured with the use of sieves.

The term "pressing" refers to the process where is a liquid is extracted from a raw material with the aid of a press. Within the context of the present invention, a liquid (e.g., oil extract of *cannabis*) is extracted from *cannabis* biomass (which is soaked in an edible oil), with the aid of a press. The press will include one or more pairs of opposing facing plates. With each pair of plates, the plate applies a force to the opposing plate, thereby releasing the oil extract of *cannabis* from the *cannabis* biomass. The press can include, e.g., a single pair of opposing facing plates. Alternatively, the press can include multiple (e.g., 2, 3, or 4) pairs of opposing facing plates. Each plate will typically be planar (flat), or substantially planar (flat). This will allow each pair of plates to come into full contact with each other, and upon the applied force, to effectively release the oil extract of cannabis from the cannabis biomass. The plates will also have a suitable two-dimensional profile. For example, in specific embodiments, each plate will have each of a length and width independently of up to 24 inches. Specifically, in specific embodiments, each plate will independently have a length of up to 24 inches, up to 18 inches, up to 12 inches, up to 9 inches, or up to 6 inches. Additionally, in specific embodiments, each plate will independently have a width of up to 24 inches, up to 18 inches, up to 12 inches, up to 9 inches, or up to 6 inches. Likewise, the plates will also have a suitable surface area. Specifically, in specific embodiments, each plate will independently have a surface area of up to 576 in$^2$, up to 324 in$^2$, up to 144 in$^2$, up to 81 in$^2$, or up to 36 in$^2$.

As used herein, "spent cannabis" refers to the remaining cannabis biomass after the oil extract of cannabis has been removed therefrom.

As used herein, "planar" or "flat" refers to an article having a dimension that lies substantially in a single plane. The article would have an absence of any slope or curvature. Within the context of the present invention, the plates can be flat, such that they have a relatively smooth, even surface.

One or more enclosures can be used for use in the method of the present invention. The enclosure can include an article that will readily allow for the oil extract of cannabis to separate from the cannabis biomass, upon the application of force by the press. For example, the article can have a mesh or screen on one or more surfaces, to allow for the oil extract of cannabis to separate from the cannabis biomass. Specifically, the enclosure can be a food grade mesh nylon bag, or an FDA nylon stitching rosin press filter bag. The enclosure can have any suitable dimension. In specific embodiments, the enclosure can be a food grade mesh nylon bag or FDA nylon stitching rosin press filter bag having a length of up to 20" and a width of up to 15". Additionally, the nylon mesh bag can be 36 or 73 microns. One particularly suitable bag is commercially available from Beijing PFM Screen Trading Co., Ltd. (Hebei, China).

Upon the separating of the spent cannabis biomass and the oil extract of cannabis, the oil extract of cannabis can be collected in a suitable receptacle or container (e.g., jug, jar, bottle, pan, tray, cup, bucket, reservoir, etc.). In specific embodiments, the oil extract of cannabis from a single batch can be collected in the receptacle. In alternative embodiments, the oil extract of cannabis from multiple batches can be collected in the receptacle, where the receptacle is regularly emptied, and the multiple oil extracts of cannabis are collected.

In specific embodiments, the method for obtaining an oil extract of cannabis as described herein can be carried out in a batch mode (alternatively referred to as "batch production"). As used herein, "batch mode" refers to a method of manufacturing where the products are made as specified groups or amounts, within a time frame. A batch can go through a series of steps in a large manufacturing process to make the final desired product. Batch production is used for many types of manufacturing that may need smaller amounts of production at a time to ensure specific quality standards or changes in the process. This is opposed to large mass production or continuous production methods where the product or process does not need to be checked or changed as frequently or periodically. Within the context of the present invention, a batch production can be carried out on a scale of up to about 50 ounces of cannabis biomass (e.g., up to 32 ounces of cannabis dry trim, kief, or bubble hash and up to 32 ounces of cannabis plant and flower). Additionally, a batch production can be carried out within a relatively short period of time (e.g., within 75 minutes).

The method for obtaining an oil extract of cannabis as described herein can optionally include a subsequent purification of the oil extract of cannabis. As used herein the term "purifying" (and purification) refers to a process of physical separation of a chemical substance of interest from foreign or contaminating substances. Within the context of the present invention, foreign or contaminating substances desired to be removed can include, e.g., pesticides, heavy metals, microbials, volatile organic compounds (VOCs), and chlorophylls.

Pure results of a successful purification process are termed an "isolate." The following non-exhaustive list of chemical purification methods can be employed within the context of the present invention: filtration, centrifugation, evaporation, liquid-liquid extraction, crystallization, recrystallization, trituration, adsorption, chromatography, and distillation.

As used herein, "filtration" refers to a mechanical method to separate solids from liquids or gases by passing the feed stream through a porous sheet such as a cloth or membrane, which retains the solids and allows the liquid to pass through.

As used herein, "centrifugation" refers to a process that uses an electric motor to spin a vessel of fluid at high speed to make heavier components settle to the bottom of the vessel.

As used herein, "evaporation" refers to a process which removes volatile liquids from non-volatile solutes, which cannot be done through filtration due to the small size of the substances.

As used herein, "liquid-liquid extraction" refers to a process which removes an impurity or recovers a desired product by dissolving the crude material in a solvent in which other components of the feed material are soluble.

As used herein, "crystallization" refers to a process which separates a product from a liquid feed stream, often in extremely pure form, by cooling the feed stream or adding precipitants that lower the solubility of the desired product so that it forms crystals. The pure solid crystals are then separated from the remaining liquor by filtration or centrifugation.

As used herein, "recrystallization" refers to a process in which a desired solid (crystalline) product is dissolved in a very pure solvent, and then crystallized, and the crystals recovered, in order to improve and/or verify their purity.

As used herein, "trituration" refers to as process that removes highly soluble impurities from usually solid insoluble material by rinsing it with an appropriate solvent.

As used herein, "adsorption" refers to a process that removes a soluble impurity from a feed stream by trapping it on the surface of a solid material, such as activated carbon, that forms strong non-covalent chemical bonds with the impurity. Within the context of the present invention, carbon black is a substance suitable for adsorption.

As used herein, "chromatography" refers to a process that employs continuous adsorption and desorption on a packed bed of a solid to purify multiple components of a single feed stream. In a laboratory setting, mixture of dissolved materials are typically fed using a solvent into a column packed with an appropriate adsorbent, and due to different affinities for solvent versus adsorbent the components in the original mixture exit the column in the moving phase at different rates, which thus allows to selectively collect desired materials out of the initial mixture.

As used herein, "distillation" refers to a process that separates one or more volatile liquids on the basis of their relative volatilities. There are several types of distillation: simple distillation, fractional distillation, steam distillation etc.

Specific Embodiments

The specific embodiments describing the subject matter provided below are for illustration purposes only, and do not otherwise limit the scope of the disclosed subject matter, as defined by the claims.

In specific embodiments, the present invention provides for a method for obtaining an oil extract of *cannabis*, wherein the method includes: (a) contacting, in an enclosure, *cannabis* biomass and an edible oil; (b) pressing the enclosure and contents therein, sufficient to release from the *cannabis* biomass into the edible oil, one or more cannabinoids, one or more terpenes, or a combination thereof, to provide spent *cannabis* and an oil extract of *cannabis*; and (c) separating the spent *cannabis* biomass and the oil extract of *cannabis*.

In specific embodiments, the method further includes before the contacting in step (a), the step of reducing the size of the *cannabis* biomass.

In specific embodiments, the method further includes after the contacting in step (a) and before the pressing in step (b), the step of steeping the *cannabis* biomass and the edible oil.

In specific embodiments, the method further includes after the separating in step (c), the step of purifying the oil extract of *cannabis*.

In specific embodiments, the present invention provides for a method for obtaining an oil extract of *cannabis*, wherein the method includes: (a) reducing the size of *cannabis* biomass; (b) contacting, in an enclosure, *cannabis* biomass and an edible oil; (c) steeping the *cannabis* biomass and the edible oil; (d) pressing the enclosure and contents therein, sufficient to release from the *cannabis* biomass into the edible oil, one or more cannabinoids, one or more terpenes, or a combination thereof, to provide spent *cannabis* and an oil extract of *cannabis*; (e) separating the spent *cannabis* biomass and the oil extract of *cannabis*; and (f) purifying the oil extract of *cannabis*.

In specific embodiments, relative to the *cannabis* biomass, the oil extract of *cannabis* is enriched with one or more cannabinoids.

In specific embodiments, on a weight percentage basis, the oil extract of *cannabis* contains at least 25% more cannabinoids than the *cannabis* biomass.

In specific embodiments, on a weight percentage basis, the oil extract of *cannabis* contains at least 50% more cannabinoids than the *cannabis* biomass.

In specific embodiments, on a weight percentage basis, the oil extract of *cannabis* contains at least 100% more cannabinoids than the *cannabis* biomass.

In specific embodiments, on a weight percentage basis, the oil extract of *cannabis* contains at least 150% more cannabinoids than the *cannabis* biomass.

In specific embodiments, on a weight percentage basis, the oil extract of *cannabis* contains at least 200% more cannabinoids than the *cannabis* biomass.

In specific embodiments, relative to the *cannabis* biomass, the oil extract of *cannabis* is enriched with one or more terpenes.

In specific embodiments, relative to the *cannabis* biomass, the oil extract of *cannabis* contains less pesticides, heavy metals, microbials, volatile organic compounds (VOCs), or chlorophylls.

In specific embodiments, relative to the *cannabis* biomass, the oil extract of *cannabis* contains less pesticides.

In specific embodiments, on a weight percentage basis, relative to the *cannabis* biomass, the oil extract of *cannabis* contains at least 10% less pesticides.

In specific embodiments, relative to the *cannabis* biomass, the oil extract of *cannabis* contains less heavy metals.

In specific embodiments, on a weight percentage basis, relative to the *cannabis* biomass, the oil extract of *cannabis* contains at least 10% less heavy metals.

In specific embodiments, relative to the *cannabis* biomass, the oil extract of *cannabis* contains less microbials.

In specific embodiments, on a weight percentage basis, relative to the *cannabis* biomass, the oil extract of *cannabis* contains at least 10% less microbials.

In specific embodiments, relative to the *cannabis* biomass, the oil extract of *cannabis* contains less volatile organic compounds (VOCs).

In specific embodiments, on a weight percentage basis, relative to the *cannabis* biomass, the oil extract of *cannabis* contains at least 10% less volatile organic compounds (VOCs).

In specific embodiments, relative to the *cannabis* biomass, the oil extract of *cannabis* contains at least 10% less chlorophylls.

In specific embodiments, on a weight percentage basis, relative to the *cannabis* biomass, the oil extract of *cannabis* contains at least 10% less chlorophylls.

In specific embodiments, relative to the *cannabis* biomass, the oil extract of *cannabis* contains less pesticides, heavy metals, microbials, volatile organic compounds (VOCs), and chlorophylls.

In specific embodiments, the oil extract of *cannabis* includes one or more cannabinoids, one or more terpenes, or a combination thereof.

In specific embodiments, the process is carried out in a batch mode.

In specific embodiments, the process is carried out in a batch mode wherein at least 20 ounces of *cannabis* biomass is employed per batch.

In specific embodiments, the process is carried out in a batch mode wherein at least 30 ounces of *cannabis* biomass is employed per batch.

In specific embodiments, the process is carried out in a batch mode wherein at least 40 ounces of *cannabis* biomass is employed per batch.

In specific embodiments, the process is carried out in a batch mode wherein 10-40 ounces of *cannabis* biomass is employed per batch.

In specific embodiments, the process is carried out in a batch mode wherein 20-40 ounces of *cannabis* biomass is employed per batch.

In specific embodiments, the oil extract of *cannabis* obtained therein is a full-spectrum extract of *cannabis*.

In specific embodiments, the oil extract of *cannabis* obtained therein is a broad-spectrum extract of *cannabis*.

In specific embodiments, the oil extract of *cannabis* obtained therein is a full-spectrum extract of *cannabis* or a broad-spectrum extract of *cannabis*.

In specific embodiments, the enclosure is a food grade 73-micron filter mesh nylon bag.

In specific embodiments, the enclosure is a food grade 36-micron filter mesh nylon bag.

In specific embodiments, the edible oil includes at least one of Grade 1 edible oil, Grade 2 edible oil, Grade 3 edible oil, and Grade 4 edible oil.

In specific embodiments, the edible oil is a plant-based oil.

In specific embodiments, the edible oil includes at least one of Coconut oil, Corn oil, Canola oil, Cottonseed oil, Olive oil, Palm oil, Peanut oil, Rapeseed oil, Safflower oil, Sesame oil, Soybean oil, Sunflower oil, Almond oil, Beech nut oil, Brazil nut oil, Cashew oil, Hazelnut oil, Macadamia oil, Mongongo nut oil, Pecan oil, Pine nut oil, Pistachio oil, Walnut oil, Pumpkin seed oil, Grapefruit seed oil, Lemon oil, Orange oil, Bitter gourd oil, Bottle gourd oil, Buffalo gourd oil, Butternut squash seed oil, Egusi seed oil, Pumpkin seed oil, Watermelon seed oil, Açaí oil, Black seed oil, Blackcurrant seed oil, Borage seed oil, Evening primrose oil, Flaxseed oil, Amaranth oil, Apricot oil, Apple seed oil, Argan oil, Avocado oil, Babassu oil, Ben oil, Borneo tallow nut oil, Cape chestnut oil, Carob pod oil, Cocoa butter, Cocklebur oil, Cohune oil, Coriander seed oil, Date seed oil, Dika oil, False flax oil, Grape seed oil, Hemp oil, Kapok seed oil, Kenaf seed oil, Lallemantia oil, Mafura oil, Marula oil, Meadowfoam seed oil, Mustard oil, Niger seed oil, Poppyseed oil, Nutmeg butter, Okra seed oil, Papaya seed oil, Perilla seed oil, Persimmon seed oil, Pequi oil, Pili nut oil, Pomegranate seed oil, Poppyseed oil, Pracaxi oil, Virgin pracaxi oil, Prune kernel oil, Quinoa oil, Ramtil oil, Rice bran oil, Royle oil, Shea butter, Sacha inchi oil, Sapote oil, Seje oil, Taramira oil, Tea seed oil (Camellia oil), Thistle oil, Tigernut oil (or nut-sedge oil), Tobacco seed oil, Tomato seed oil, and Wheat germ oil.

In specific embodiments, the edible oil includes at least one of virgin coconut oil (VCO), avocado oil, medium chain triglycerides (MCTs), olive oil, hemp see oil, and vegetable oil.

In specific embodiments, the edible oil and *cannabis* biomass are present in the contacting step in a weight ratio of at least 2:1.

In specific embodiments, the edible oil and *cannabis* biomass are present in the contacting step in a weight ratio of up to 7:1.

In specific embodiments, the edible oil and *cannabis* biomass are present in the contacting step in a weight ratio of 2:1 to 7:1.

In specific embodiments, the edible oil and *cannabis* biomass are present in the contacting step in a weight ratio of 3:1 to 6:1.

In specific embodiments, the edible oil and *cannabis* biomass are present in the contacting step for up to 24 hours prior to the pressing step.

In specific embodiments, the edible oil and *cannabis* biomass are present in the contacting step for up to 12 hours prior to the pressing step.

In specific embodiments, the edible oil and *cannabis* biomass are present in the contacting step for up to 8 hours prior to the pressing step.

In specific embodiments, the edible oil and *cannabis* biomass are present in the contacting step for up to 4 hours prior to the pressing step.

In specific embodiments, the edible oil and *cannabis* biomass are present in the contacting step for up to 2 hours prior to the pressing step.

In specific embodiments, the edible oil and *cannabis* biomass are present in the contacting step for 5-25 minutes prior to the pressing step.

In specific embodiments, the edible oil and *cannabis* biomass are present in the contacting step for 5-15 minutes prior to the pressing step.

In specific embodiments, after the contacting step and before the pressing step, the method includes the step of steeping the *cannabis* biomass and the edible oil.

In specific embodiments, after the contacting step and before the pressing step, the method includes the step of steeping, at a temperature of up to 180° C., the *cannabis* biomass and the edible oil.

In specific embodiments, after the contacting step and before the pressing step, the method includes the step of steeping, at a temperature of up to 150° C., the *cannabis* biomass and the edible oil.

In specific embodiments, after the contacting step and before the pressing step, the method includes the step of steeping, at a temperature of up to 120° C., the *cannabis* biomass and the edible oil.

In specific embodiments, after the contacting step and before the pressing step, the method includes the step of steeping, at a temperature of up to 110° C., the *cannabis* biomass and the edible oil.

In specific embodiments, after the contacting step and before the pressing step, the method includes the step of steeping, at a temperature of up to 100° C., the *cannabis* biomass and the edible oil.

In specific embodiments, after the contacting step and before the pressing step, the method includes the step of steeping, at a temperature of at least 50° C., the *cannabis* biomass and the edible oil.

In specific embodiments, after the contacting step and before the pressing step, the method includes the step of steeping, at a temperature of at least 60° C., the *cannabis* biomass and the edible oil.

In specific embodiments, after the contacting step and before the pressing step, the method includes the step of steeping, at a temperature of at least 70° C., the *cannabis* biomass and the edible oil.

In specific embodiments, after the contacting step and before the pressing step, the method includes the step of steeping, at a temperature of at least 80° C., the *cannabis* biomass and the edible oil.

In specific embodiments, after the contacting step and before the pressing step, the method includes the step of steeping, at a temperature of at least 90° C., the *cannabis* biomass and the edible oil.

In specific embodiments, after the contacting step and before the pressing step, the method includes the step of steeping, at a temperature of at least 100° C., the *cannabis* biomass and the edible oil.

In specific embodiments, the pressing is carried out at an elevated temperature.

In specific embodiments, the pressing is carried out at a temperature of up to 110° C.

In specific embodiments, the pressing is carried out at a temperature of at least 65° C.

In specific embodiments, the pressing is carried out at a temperature of 65-110° C.

In specific embodiments, the pressing is a cold press, such that the pressing is carried out at a temperature of 19-25° C.

In specific embodiments, the pressing is carried out for a period of time of at least 5 seconds.

In specific embodiments, the pressing is carried out for a period of time of at least 10 seconds.

In specific embodiments, the pressing is carried out for a period of time of at least 30 seconds.

In specific embodiments, the pressing is carried out for a period of time of at least 1 minute.

In specific embodiments, the pressing is carried out for a period of time of 5 minutes.

In specific embodiments, the pressing is carried out at pressure of up to 100,000 psi.

In specific embodiments, the pressing is carried out at pressure of up to 75,000 psi.

In specific embodiments, the pressing is carried out at pressure of at least 1,000 psi.

In specific embodiments, the pressing is carried out at pressure of at least 5,000 psi.

In specific embodiments, the pressing is carried out at pressure of at least 7,500 psi.

In specific embodiments, the pressing is carried out at pressure of at least 10,000 psi.

In specific embodiments, the pressing is carried out at pressure of at least 15,000 psi.

In specific embodiments, the pressing is carried out at pressure of at least 20,000 psi.

In specific embodiments, the pressing is carried out at pressure of at least 25,000 psi.

In specific embodiments, the pressing is carried out at pressure of at least 50,000 psi.

In specific embodiments, the pressing is carried out at pressure of 1,000-100,000 psi.

In specific embodiments, the pressing is carried out at pressure of 25,000-100,000 psi.

In specific embodiments, the pressing is carried out at pressure of 25,000-75,000 psi.

In specific embodiments, the pressing is carried out between one or more pairs of plates.

In specific embodiments, the pressing is carried out between one pair of plates.

In specific embodiments, the pressing is carried out between multiple (e.g., 2, 3, 4, etc.) pairs of plates.

In specific embodiments, the pressing is carried out between two plates each independently having a surface area of up to 325 in$^2$.

In specific embodiments, the pressing is carried out between two plates each independently having a surface area of up to 290 in$^2$.

In specific embodiments, the pressing is carried out between two plates each independently having a surface area of up to 260 in$^2$.

In specific embodiments, the pressing is carried out between two plates each independently having a surface area of up to 225 in$^2$.

In specific embodiments, the pressing is carried out between two plates each independently having a surface area of up to 200 in$^2$.

In specific embodiments, the pressing is carried out between two plates each independently having a surface area of up to 170 in$^2$.

In specific embodiments, the pressing is carried out between two plates each independently having a surface area of up to 145 in$^2$.

In specific embodiments, the pressing is carried out between two plates each independently having a surface area of up to 121 in$^2$.

In specific embodiments, the pressing is carried out between two plates each independently having a surface area of up to 100 in$^2$.

In specific embodiments, the pressing is carried out between two plates each independently having a surface area of 25-325 in$^2$.

In specific embodiments, the pressing is carried out between two plates each independently having a surface area of 25-225 in$^2$.

In specific embodiments, the pressing is carried out between two plates each independently having a surface area of 25-125 in$^2$.

In specific embodiments, the pressing is carried out between two plates each independently having a surface area of 120±10 in$^2$.

In specific embodiments, the pressing is carried out between two plates each having a two-dimensional profile of 6"×9" to 12"×18".

In specific embodiments, the pressing is carried out between two plates each having a two-dimensional profile of 7"×10" to 11"×17".

In specific embodiments, the pressing is carried out between two plates each having a two-dimensional profile of 8"×10" to 11"×17".

In specific embodiments, the pressing is carried out between two plates each having a two-dimensional profile of 9"×12".

In specific embodiments, the separating is carried out employing filtration.

In specific embodiments, 135-160 grams of oil extract of *cannabis* is obtained, per pound of *cannabis* biomass.

In specific embodiments, up to 160 grams of oil extract of *cannabis* is obtained, per pound of *cannabis* biomass.

In specific embodiments, at least 135 grams of oil extract of *cannabis* is obtained, per pound of *cannabis* biomass.

In specific embodiments, the oil extract of *cannabis* includes up to 35 wt. % cannabinoids, terpenes, or combination thereof.

In specific embodiments, the oil extract of *cannabis* includes up to 30 wt. % cannabinoids, terpenes, or combination thereof.

In specific embodiments, the oil extract of *cannabis* includes at least 25 wt. % cannabinoids, terpenes, or combination thereof.

In specific embodiments, the oil extract of *cannabis* includes at least 30 wt. % cannabinoids, terpenes, or combination thereof.

In specific embodiments, the oil extract of *cannabis* includes 20-35 wt. % cannabinoids, terpenes, or combination thereof.

In specific embodiments, the oil extract of *cannabis* includes less than 2 wt. % CBD.

In specific embodiments, the oil extract of *cannabis* includes less than 1 wt. % CBD.

In specific embodiments, the oil extract of *cannabis* includes less than 0.5 wt. % CBD.

In specific embodiments, the oil extract of *cannabis* includes less than 0.1 wt. % CBD.

In specific embodiments, the oil extract of *cannabis* includes less than 2 wt. % THC.

In specific embodiments, the oil extract of *cannabis* includes less than 1 wt. % THC.

In specific embodiments, the oil extract of *cannabis* includes less than 0.5 wt. % THC.

In specific embodiments, the oil extract of *cannabis* includes less than 0.1 wt. % THC.

In specific embodiments, the oil extract of *cannabis* includes less than 0.1 wt. % pesticides.

In specific embodiments, the oil extract of *cannabis* includes less than 0.1 wt. % heavy metals.

In specific embodiments, the oil extract of *cannabis* includes less than 0.1 wt. % microbials.

In specific embodiments, the oil extract of *cannabis* includes less than 0.1 wt. % volatile organic compounds (VOCs).

In specific embodiments, the oil extract of *cannabis* includes less than 1 wt. % chlorophylls.

In specific embodiments, the oil extract of *cannabis* includes

| Cannabinoid | Mass (%) | Mass (mg/g) |
|---|---|---|
| THCa | 20.2% | 202.2 mg/g |
| Δ9-THC | 12.8 | 128.2 mg/g |
| Δ8-THC | <LOQ | <LOQ |
| THCV | <LOQ | <LOQ |
| CBDa | 0.1% | 1.2 mg/g |
| CBD | <LOQ | <LOQ |
| CBDV | <LOQ | <LOQ |
| CBN | 0.1% | 1.4 mg/g |
| CBC | 0.1% | 1.1 mg/g |
| CBGa | 0.6% | 5.6 mg/g |
| CBG | 0.3% | 3.3 mg/g |

In specific embodiments, the oil extract of *cannabis* is essentially free of terpenes, such that the oil extract of *cannabis* includes

| Terpene | Mass (%) | Mass (mg/g) |
|---|---|---|
| β-myrcene | 0.2% | 1.7 mg/g |
| δ-limonene | 0.1% | 1.2 mg/g |
| β-caryophyllene | 0.0% | 0.3 mg/g |
| β-pinene | 0.0% | 0.2 mg/g |
| α-pinene | 0.0% | 0.1 mg/g |
| α-terpineol | 0.0% | 0.1 mg/g |
| α-humulene | 0.0% | 0.1 mg/g |
| camphene | 0.0% | 0.0 mg/g |
| fenchone | 0.0% | 0.0 mg/g |
| terpinolene | 0.0% | 0.0 mg/g |
| α-terpinene | 0.0% | 0.0 mg/g |
| 3-carene | <LOQ | <LOQ |
| α-phellandrene | <LOQ | <LOQ |
| borneol | <LOQ | <LOQ |
| fenchol | <LOQ | <LOQ |
| ocimene | <LOQ | <LOQ |
| valencene | <LOQ | <LOQ |

In specific embodiments, the *cannabis* biomass is reduced in size (i.e., the process further includes a reducing in the size of the *cannabis* biomass).

In specific embodiments, the *cannabis* biomass is reduced in size to an average particle size of 2.5 mm or less.

In specific embodiments, the *cannabis* biomass is reduced in size such that at least 50 wt. % of the *cannabis* biomass has a particle size of 2.5 mm or less.

In specific embodiments, the *cannabis* biomass is reduced in size such that at least 75 wt. % of the *cannabis* biomass has a particle size of 2.5 mm or less.

In specific embodiments, the *cannabis* biomass is reduced in size such that at least 90 wt. % of the *cannabis* biomass has a particle size of 2.5 mm or less.

In specific embodiments, the *cannabis* biomass is reduced in size such that at least 95 wt. % of the *cannabis* biomass has a particle size of 2.5 mm or less.

In specific embodiments, the *cannabis* biomass is reduced in size to an average particle size of 2 mm or less.

In specific embodiments, the *cannabis* biomass is reduced in size such that at least 50 wt. % of the *cannabis* biomass has a particle size of 2 mm or less.

In specific embodiments, the *cannabis* biomass is reduced in size such that at least 75 wt. % of the *cannabis* biomass has a particle size of 2 mm or less.

In specific embodiments, the *cannabis* biomass is reduced in size such that at least 90 wt. % of the *cannabis* biomass has a particle size of 2 mm or less.

In specific embodiments, the *cannabis* biomass is reduced in size such that at least 95 wt. % of the *cannabis* biomass has a particle size of 2 mm or less.

In specific embodiments, the *cannabis* biomass is reduced in size prior to the contacting with the edible oil.

In specific embodiments, the *cannabis* biomass is reduced in size while contacting the edible oil.

In specific embodiments, the *cannabis* biomass is reduced in size in the absence of the edible oil.

In specific embodiments, the *cannabis* biomass is reduced in size in the presence of the edible oil.

In specific embodiments, the *cannabis* biomass is reduced in size employing at least one of blending, grinding, pulverizing, mincing, liquefying, cutting, macerating, and chopping.

In specific embodiments, the oil extract of *cannabis* is purified (i.e., the process further includes purifying the oil extract of *cannabis*).

In specific embodiments, after the separating of the oil extract of *cannabis* and the spent biomass, the oil extract of *cannabis* is purified.

In specific embodiments, the oil extract of *cannabis* is purified employing at least one of chromatography, distillation, filtration, solvent extraction, crystallization, and centrifugation.

In specific embodiments, the oil extract of *cannabis* is purified to obtain an isolate of *cannabis*.

In specific embodiments, the process further includes contacting the oil extract of *cannabis* with carbon black and separating the carbon black from the oil extract of *cannabis*.

In specific embodiments, the process further includes contacting the oil extract of *cannabis* with carbon black and separating the carbon black from the oil extract of *cannabis*; wherein the carbon black is carbon black c-6, carbon black c-18, or a combination thereof.

In specific embodiments, the process further includes contacting the oil extract of *cannabis* with carbon black in an amount of 0.5±0.2 grams of carbon black per 100 g of the oil extract of *cannabis*; and separating the carbon black from the oil extract of *cannabis*.

In specific embodiments, the process further includes contacting the oil extract of *cannabis* with carbon black in an amount of 0.5±0.1 grams of carbon black per 100 g of the oil extract of *cannabis*; and separating the carbon black from the oil extract of *cannabis*.

In specific embodiments, the process further includes contacting the oil extract of *cannabis* with carbon black in an amount of 0.5 grams of carbon black per 100 g of the oil extract of *cannabis*; and separating the carbon black from the oil extract of *cannabis*.

In specific embodiments, the process is carried out in the absence of a polar liquid organic solvent.

In specific embodiments, the process is carried out in the absence of a polar liquid organic solvent containing at least one of chloroform, methylene chloride, ethyl acetate, ethanol, and methanol.

In specific embodiments, the process is carried out in the absence of volatile organic compound (VOC) solvent.

In specific embodiments, the process is carried out in the absence of a supercritical fluid extraction solvent.

In specific embodiments, the process is carried out in the absence of a supercritical fluid extraction solvent containing at least one of carbon dioxide, butane, propane, and ethanol.

In specific embodiments, the process is carried out in the absence of a pressurized vessel.

In specific embodiments, the oil extract of *cannabis* includes no more than 1 wt. % of each of pesticides, heavy metals, microbials, and volatile organic compounds (VOCs).

In specific embodiments, the oil extract of *cannabis* includes no more than 0.5 wt. % of each of pesticides, heavy metals, microbials, and volatile organic compounds (VOCs).

In specific embodiments, the oil extract of *cannabis* includes no more than 0.1 wt. % of each of pesticides, heavy metals, microbials, and volatile organic compounds (VOCs).

In specific embodiments, the oil extract of *cannabis* includes no more than 5 wt. % in the aggregate of terpenes and CBD.

In specific embodiments, the oil extract of *cannabis* includes no more than 2.5 wt. % in the aggregate of terpenes and CBD.

In specific embodiments, the oil extract of *cannabis* includes no more than 1 wt. % in the aggregate of terpenes and CBD.

In specific embodiments, the oil extract of *cannabis* includes no more than 0.5 wt. % in the aggregate of terpenes and CBD.

In specific embodiments, the oil extract of *cannabis* is a THC isolate.

In specific embodiments, the oil extract of *cannabis* is a CBD isolate.

In specific embodiments, the oil extract of *cannabis* is a phytocannabinoid rich hemp oil.

In specific embodiments, the oil extract of *cannabis* is a broad-spectrum isolate of *cannabis*.

In specific embodiments, the oil extract of *cannabis* is a full-spectrum isolate of *cannabis*.

In specific embodiments, the process is carried out in less than 150 minutes.

In specific embodiments, the process is carried out in less than 120 minutes.

In specific embodiments, the process is carried out in less than 90 minutes.

In specific embodiments, the process is carried out in less than 75 minutes.

In specific embodiments, the oil extract of *cannabis* is suitable for oral administration to a human.

In specific embodiments, the oil extract of *cannabis* is suitable for topical administration to a human.

Enumerated Embodiments

Specific enumerated embodiments <1> to <64> provided below are for illustration purposes only, and do not otherwise limit the scope of the disclosed subject matter, as defined by the claims. These enumerated embodiments encompass all combinations, sub-combinations, and multiply referenced (e.g., multiply dependent) combinations described therein.

<Embodiment 1> The present invention provides for a method for obtaining an oil extract of *cannabis*, the method including:
(a) contacting, in an enclosure, *cannabis* biomass and an edible oil,
(b) pressing the enclosure and contents therein, sufficient to release from the *cannabis* biomass into the edible oil, one or more cannabinoids, one or more terpenes, or a combination thereof, to provide spent *cannabis* and an oil extract of *cannabis*, and
(c) separating the spent *cannabis* biomass and the oil extract of *cannabis*,
wherein,
the oil extract of *cannabis* includes one or more cannabinoids, one or more terpenes, or a combination thereof.

<Embodiment 2> The present invention provides for the method of embodiment <1>, carried out in a batch mode wherein up to 40 ounces of *cannabis* biomass is employed per batch.

<Embodiment 3> The present invention provides for the method of embodiment <1>, carried out in a batch mode wherein at least 20 ounces of *cannabis* biomass is employed per batch.

<Embodiment 4> The present invention provides for the method of embodiment <1>, carried out in a batch mode wherein 20-40 ounces of *cannabis* biomass is employed per batch.

<Embodiment 5> The present invention provides for the method of any one or more of the above embodiments, wherein the oil extract of *cannabis* obtained therein is a full-spectrum extract of *cannabis*.

<Embodiment 6> The present invention provides for the method of any one or more of the above embodiments, wherein the oil extract of *cannabis* obtained therein is a broad-spectrum extract of *cannabis*.

<Embodiment 7> The present invention provides for the method of any one or more of the above embodiments, wherein in step (a), the enclosure is a food grade 73-micron filter mesh nylon bag.

<Embodiment 8> The present invention provides for the method of any one or more of the above embodiments, wherein in step (a), the enclosure is a food grade 36-micron filter mesh nylon bag.

<Embodiment 9> The present invention provides for the method of any one or more of the above embodiments, wherein in step (a), the enclosure is an FDA nylon stitching rosin press filter bag.

<Embodiment 10> The present invention provides for the method of any one or more of the above embodiments, wherein in step (a), the *cannabis* biomass is no larger than 2.5 mm in size.

<Embodiment 11> The present invention provides for the method of any one or more of the above embodiments, wherein in step (a), the oil is an edible oil.

<Embodiment 12> The present invention provides for the method of any one or more of the above embodiments, wherein in step (a), the edible oil is a Grade 1 edible oil, Grade 2 edible oil, Grade 3 edible oil, Grade 4 edible oil, or any combination thereof.

<Embodiment 13> The present invention provides for the method of any one or more of the above embodiments, wherein in step (a), the edible oil includes at least one of Coconut oil, Corn oil, Canola oil, Cottonseed oil, Olive oil, Palm oil, Peanut oil, Rapeseed oil, Safflower oil, Sesame oil, Soybean oil, Sunflower oil, Almond oil, Beech nut oil, Brazil nut oil, Cashew oil, Hazelnut oil, Macadamia oil, Mongongo nut oil, Pecan oil, Pine nut oil, Pistachio oil, Walnut oil, Pumpkin seed oil, Grapefruit seed oil, Lemon oil, Orange oil, Bitter gourd oil, Bottle gourd oil, Buffalo gourd oil, Butternut squash seed oil, Egusi seed oil, Pumpkin seed oil, Watermelon seed oil, Açaí oil, Black seed oil, Blackcurrant seed oil, Borage seed oil, Evening primrose oil, Flaxseed oil, Amaranth oil, Apricot oil, Apple seed oil, Argan oil, Avocado oil, Babassu oil, Ben oil, Borneo tallow nut oil, Cape chestnut oil, Carob pod oil, Cocoa butter, Cocklebur oil, Cohune oil, Coriander seed oil, Date seed oil, Dika oil, False flax oil, Grape seed oil, Hemp oil, Kapok seed oil, Kenaf seed oil, Lallemantia oil, Mafura oil, Marula oil, Meadowfoam seed oil, Mustard oil, Niger seed oil, Poppyseed oil, Nutmeg butter, Okra seed oil, Papaya seed oil, Perilla seed oil, Persimmon seed oil, Pequi oil, Pili nut oil, Pomegranate seed oil, Poppyseed oil, Pracaxi oil, Virgin pracaxi oil, Prune kernel oil, Quinoa oil, Ramtil oil, Rice bran oil, Royle oil, Shea butter, Sacha inchi oil, Sapote oil, Seje oil, Taramira oil, Tea seed oil (Camellia oil), Thistle oil, Tigernut oil (or nut-sedge oil), Tobacco seed oil, Tomato seed oil, and Wheat germ oil.

<Embodiment 14> The present invention provides for the method of any one or more of the above embodiments, wherein in step (a), the edible oil includes virgin coconut oil (VCO), avocado oil, medium chain triglycerides (MCTs), olive oil, hemp see oil, vegetable oil, or any combination thereof.

<Embodiment 15> The present invention provides for the method of any one or more of the above embodiments, wherein in step (a), the edible oil and *cannabis* biomass are present in a weight ratio of 2:1 to 7:1.

<Embodiment 16> The present invention provides for the method of any one or more of the above embodiments, wherein in step (a), the edible oil and *cannabis* biomass are in contact for up to 24 hours prior to the pressing in step (b).

<Embodiment 17> The present invention provides for the method of any one or more of the above embodiments, wherein in step (a), the edible oil and *cannabis* biomass are in contact for 5-25 minutes prior to the pressing in step (b).

<Embodiment 18> The present invention provides for the method of any one or more of the above embodiments, wherein in step (a), the edible oil and *cannabis* biomass are steeped at a temperature below 110° C., prior to the pressing in step (b).

<Embodiment 19> The present invention provides for the method of any one or more of the above embodiments, wherein in step (b), the pressing is carried out at an elevated temperature.

<Embodiment 20> The present invention provides for the method of any one or more of the above embodiments, wherein in step (b), the pressing is carried out at a temperature of 65-110° C.

<Embodiment 21> The present invention provides for the method of any one or more of the above embodiments, wherein in step (b), the pressing is a cold press, such that the pressing is carried out at a temperature of 19-25° C.

<Embodiment 22> The present invention provides for the method of any one or more of the above embodiments, wherein in step (b), the pressing is carried out for a period of time of 5 minutes.

<Embodiment 23> The present invention provides for the method of any one or more of the above embodiments, wherein in step (b), the pressing is carried out to a pressure of up to 100,000 psi.

<Embodiment 24> The present invention provides for the method of any one or more of the above embodiments, wherein in step (b), the pressing is carried out between two plates each having a surface area of up to 225 in$^2$.

<Embodiment 25> The present invention provides for the method of any one or more of the above embodiments, wherein in step (b), the pressing is carried out between two plates each having a surface area of 120±10 in$^2$.

<Embodiment 26> The present invention provides for the method of any one or more of the above embodiments, wherein in step (b), the pressing is carried out between two plates each having a two-dimensional profile of 6"×9" to 12"×18".

<Embodiment 27> The present invention provides for the method of any one or more of the above embodiments, wherein in step (b), the pressing is carried out between two plates each having a two-dimensional profile of 9"×12".

<Embodiment 28> The present invention provides for the method of any one or more of the above embodiments, wherein in step (c), the separating is carried out employing filtration.

<Embodiment 29> The present invention provides for the method of any one or more of the above embodiments, wherein 135-160 grams of oil extract of *cannabis* is obtained, per pound of *cannabis* biomass.

<Embodiment 30> The present invention provides for the method of any one or more of the above embodiments, wherein the oil extract of *cannabis* includes up to 35 wt. % cannabinoids, terpenes, or combination thereof.

<Embodiment 31> The present invention provides for the method of any one or more of the above embodiments, wherein the oil extract of *cannabis* includes up to 30.5 wt. % total THC.

<Embodiment 32> The present invention provides for the method of any one or more of the above embodiments, wherein the oil extract of *cannabis* includes less than 1 wt. % CBD.

<Embodiment 33> The present invention provides for the method of any one or more of the above embodiments, wherein the oil extract of *cannabis* includes less than 0.1 wt. % pesticides.

<Embodiment 34> The present invention provides for the method of any one or more of the above embodiments, wherein the oil extract of *cannabis* includes less than 0.1 wt. % heavy metals.

<Embodiment 35> The present invention provides for the method of any one or more of the above embodiments, wherein the oil extract of *cannabis* includes less than 0.1 wt. % microbials.

<Embodiment 36> The present invention provides for the method of any one or more of the above embodiments, wherein the oil extract of *cannabis* includes less than 0.1 wt. % volatile organic compounds (VOCs).

<Embodiment 37> The present invention provides for the method of any one or more of the above embodiments, wherein the oil extract of *cannabis* includes less than 1 wt. % chlorophylls.

<Embodiment 38> The present invention provides for the method of any one or more of the above embodiments, wherein the oil extract of *cannabis* includes cannabinoids, such that the oil extract of *cannabis* includes

| Cannabinoid | Mass (%) | Mass (mg/g) |
| --- | --- | --- |
| THCa | 20.2% | 202.2 mg/g |
| Δ9-THC | 12.8 | 128.2 mg/g |
| Δ8-THC | <LOQ | <LOQ |
| THCV | <LOQ | <LOQ |
| CBDa | 0.1% | 1.2 mg/g |
| CBD | <LOQ | <LOQ |
| CBDV | <LOQ | <LOQ |
| CBN | 0.1% | 1.4 mg/g |
| CBC | 0.1% | 1.1 mg/g |
| CBGa | 0.6% | 5.6 mg/g |
| CBG | 0.3% | 3.3 mg/g |

<Embodiment 39> The present invention provides for the method of any one or more of the above embodiments, wherein the oil extract of *cannabis* is essentially free of terpenes, such that the oil extract of *cannabis* includes

| Terpene | Mass (%) | Mass (mg/g) |
| --- | --- | --- |
| β-myrcene | 0.2% | 1.7 mg/g |
| δ-limonene | 0.1% | 1.2 mg/g |
| β-caryophyllene | 0.0% | 0.3 mg/g |
| β-pinene | 0.0% | 0.2 mg/g |
| α-pinene | 0.0% | 0.1 mg/g |
| α-terpineol | 0.0% | 0.1 mg/g |
| α-humulene | 0.0% | 0.1 mg/g |
| camphene | 0.0% | 0.0 mg/g |
| fenchone | 0.0% | 0.0 mg/g |
| terpinolene | 0.0% | 0.0 mg/g |
| α-terpinene | 0.0% | 0.0 mg/g |
| 3-carene | <LOQ | <LOQ |
| α-phellandrene | <LOQ | <LOQ |
| borneol | <LOQ | <LOQ |
| fenchol | <LOQ | <LOQ |
| ocimene | <LOQ | <LOQ |
| valencene | <LOQ | <LOQ |

<Embodiment 40> The present invention provides for the method of any one or more of the above embodiments, further including before step (a), reducing the size of the *cannabis* biomass to an average particle size of 2 mm or less.

<Embodiment 41> The present invention provides for the method of any one or more of the above embodiments, further including before step (a), reducing the size of the *cannabis* biomass while present in the edible oil.

<Embodiment 42> The present invention provides for the method of any one or more of the above embodiments, further including before step (a), reducing the size of the *cannabis* biomass in the absence of the edible oil.

<Embodiment 43> The present invention provides for the method of any one or more of the above embodiments, further including before step (a), reducing the size of the *cannabis* biomass including blending, grinding, pulverizing, mincing, liquefying, cutting, macerating, chopping, or any combination thereof.

<Embodiment 44> The present invention provides for the method of any one or more of the above embodiments, further including after step (c), purifying the oil extract of *cannabis*.

<Embodiment 45> The present invention provides for the method of any one or more of the above embodiments, further including after step (c), purifying the oil extract of *cannabis* employing at least one of chromatography, distillation, filtration, solvent extraction, crystallization, and centrifugation.

<Embodiment 46> The present invention provides for the method of any one or more of the above embodiments, further including after step (c), purifying the oil extract of *cannabis* to obtain an isolate of *cannabis*.

<Embodiment 47> The present invention provides for the method of any one or more of the above embodiments, further including after step (c), contacting the oil extract of *cannabis* with carbon black and separating the carbon black from the oil extract of *cannabis*; wherein the carbon black is carbon black c-6, carbon black c-18, or a combination thereof.

<Embodiment 48> The present invention provides for the method of any one or more of the above embodiments, further including after step (c), contacting the oil extract of *cannabis* with carbon black in an amount of 0.5 grams of carbon black per 100 g of the oil extract of *cannabis*, and separating the carbon black from the oil extract of *cannabis*; wherein the carbon black is carbon black c-6, carbon black c-18, or a combination thereof.

<Embodiment 49> The present invention provides for the method of any one or more of the above embodiments, which is carried out in the absence of a polar liquid organic solvent.

<Embodiment 50> The present invention provides for the method of any one or more of the above embodiments, which is carried out in the absence of a polar liquid organic solvent including chloroform, methylene chloride, ethyl acetate, ethanol, methanol, or any combination thereof.

<Embodiment 51> The present invention provides for the method of any one or more of the above embodiments, which is carried out in the absence of volatile organic compound (VOC) solvent.

<Embodiment 52> The present invention provides for the method of any one or more of the above embodiments, which is carried out in the absence of a supercritical fluid extraction solvent.

<Embodiment 53> The present invention provides for the method of any one or more of the above embodiments, which is carried out in the absence of a supercritical fluid extraction solvent including carbon dioxide, butane, propane, ethanol, or any combination thereof.

<Embodiment 54> The present invention provides for the method of any one or more of the above embodiments, which is carried out in the absence of a pressurized vessel.

<Embodiment 55> The present invention provides for the method of any one or more of the above embodiments, wherein the oil extract of *cannabis* includes no more than 0.1 wt. % of each of pesticides, heavy metals, microbials, and volatile organic compounds (VOCs).

<Embodiment 56> The present invention provides for the method of any one or more of the above embodiments, wherein the oil extract of *cannabis* includes no more than 1 wt. % in the aggregate of terpenes and CBD.

<Embodiment 57> The present invention provides for the method of any one or more of the above embodiments, wherein the oil extract of *cannabis* includes THC isolate.

<Embodiment 58> The present invention provides for the method of any one or more of the above embodiments, wherein the oil extract of *cannabis* includes CBD isolate.

<Embodiment 59> The present invention provides for the method of any one or more of the above embodiments, wherein the oil extract of *cannabis* includes Phytocannabinoid rich hemp oil.

<Embodiment 60> The present invention provides for the method of any one or more of the above embodiments, wherein the oil extract of *cannabis* includes full extract *cannabis* oil (FECO).

<Embodiment 61> The present invention provides for the method of any one or more of the above embodiments, carried out in less than 120 minutes.

<Embodiment 62> The present invention provides for the method of any one or more of the above embodiments, carried out in less than 90 minutes.

<Embodiment 63> The present invention provides for a method for obtaining an oil extract of *cannabis*, the method including:

(a) reducing the size of the *cannabis* biomass such that at least 50 wt. % is less than 2.5 mm,
(b) contacting, in an enclosure including a food grade mesh nylon bag, *cannabis* biomass and an edible oil,
(c) steeping the *cannabis* biomass and the edible oil,
(d) pressing between two substantially flat plates, at a temperature of up to 110° C. and a pressure of up to 100,000 psi, the enclosure and contents therein, sufficient to release from the *cannabis* biomass into the edible oil, one or more cannabinoids, one or more terpenes, or a combination thereof, to provide spent *cannabis* and an oil extract of *cannabis*, and
(e) separating the spent *cannabis* biomass and the oil extract of *cannabis*, wherein,
the edible oil and *cannabis* biomass are present in step (b) in a weight ratio of 2:1 to 7:1;
each of steps (a)-(e) is carried out in the absence of a polar liquid organic solvent;
each of steps (a)-(e) is carried out in the absence of volatile organic compound (VOC) solvent;
each of steps (a)-(e) is carried out in the absence of a supercritical fluid extraction solvent;
each of steps (a)-(e) is carried out in the absence of a pressurized vessel; and
the oil extract of *cannabis* includes 35±5 wt. % cannabinoids.

<Embodiment 64> The present invention provides for a method for obtaining an oil extract of *cannabis*, the method including:
(a) reducing the size of *cannabis* biomass;
(b) contacting, in an enclosure, *cannabis* biomass and an edible oil;
(c) steeping the *cannabis* biomass and the edible oil;
(d) pressing the enclosure and contents therein, sufficient to release from the *cannabis* biomass into the edible oil, one or more cannabinoids, one or more terpenes, or a combination thereof, to provide spent *cannabis* and an oil extract of *cannabis*;
(e) separating the spent *cannabis* biomass and the oil extract of *cannabis*; and
(f) purifying the oil extract of *cannabis*;
wherein,
the oil extract of *cannabis* includes one or more cannabinoids, one or more terpenes, or a combination thereof.

The invention claimed is:

1. A method for obtaining a purified coconut oil extract of *cannabis*, the method comprising:
(a) reducing the size of a *cannabis* biomass such that at least 90 wt. % of the *cannabis* biomass is less than 2.5 mm;
(b) contacting the *cannabis* biomass with coconut oil;
(c) steeping the *cannabis* biomass and the coconut oil;
(d) pressing between two flat plates, at a pressure of 1,000 psi-100,000 psi, the *cannabis* biomass and the coconut oil in a mesh nylon bag or rosin press filter bag, sufficient to release from the *cannabis* biomass and into the coconut oil, one or more cannabinoids, one or more terpenes, or a combination thereof, to yield spent *cannabis* and a coconut oil extract of *cannabis*;
(e) separating the spent *cannabis* biomass from the coconut oil extract of *cannabis*;
(f) collecting the coconut oil extract of *cannabis* in a receptacle;
(g) contacting the coconut oil extract of *cannabis* with carbon black in an amount of 0.5±0.2 grams of carbon black per 100 grams of the coconut oil extract of *cannabis*, to yield a purified coconut oil extract of *cannabis*; and
(h) separating the carbon black from the purified oil extract of *cannabis* to yield the purified coconut oil extract of *cannabis*, wherein the method is carried out in 90 minutes or less.

2. The method of claim 1, which is carried out in a batch mode wherein 20-40 ounces of *cannabis* biomass is employed per batch.

3. The method of claim 1, wherein the mesh bag or rosin press filter bag is a food grade 73-micron filter mesh nylon bag, a food grade 36-micron filter mesh nylon bag, or an FDA nylon stitching rosin press filter bag.

4. The method of claim 1, wherein the coconut oil and the *cannabis* biomass are present in a weight ratio of 2:1 to 7:1, respectively.

5. The method of claim 1, wherein the coconut oil and *cannabis* biomass are in contact for 5-25 minutes prior to the pressing.

6. The method of claim 1, wherein the coconut oil and the *cannabis* biomass are steeped at a temperature below 110° C., prior to the pressing.

7. The method of claim 1, wherein the pressing is carried out at an elevated temperature of 65° C.-110° C.

8. The method of claim 1, wherein the pressing is carried out for a period of time of 1-10 minutes.

9. The method of claim 1, wherein the pressing is carried out at a pressure of 10,000 psi to 100,000 psi.

10. The method of claim 1, wherein the pressing is carried out between two plates each independently having a surface area of up to 225 in.$^{2}$.

11. The method of claim 1, wherein the pressing is carried out between two plates each independently having a two-dimensional profile of 9°×12".

12. The method of claim 1, wherein each separating is carried out employing filtration.

13. The method of claim 1, wherein 135-160 grams of purified coconut oil extract of *cannabis* is obtained, per pound of *cannabis* biomass.

14. The method of claim 1, wherein the purified extract of *cannabis* consists essentially of 20-35 wt. % total THC.

15. The method of claim 1, wherein the purified coconut oil extract of *cannabis* consists essentially of: up to 35 wt. % cannabinoids, terpenes, or combination thereof, less than 0.1 wt. % pesticides, less than 0.1 wt. % heavy metals, less than 0.1 wt. % microbials, less than 0.1 wt. % volatile organic compounds, and less than 1 wt. % chlorophylls.

16. The method of claim 1, which is carried out in the absence of a polar liquid organic solvent, a volatile organic compound solvent, a supercritical fluid extraction solvent, and a pressurized supercritical fluid extraction vessel.

17. The method of claim 1, wherein the coconut oil is virgin coconut oil.

18. The method of claim 1, wherein the steeping of the *cannabis* biomass and the coconut oil is carried out at a temperature of 50° C.-180° C.

19. The method of claim 1, wherein the pressing between the two flat plates is carried out at a temperature of 20° C.-230° C.

* * * * *